（12）United States Patent
Geer

(10) Patent No.: US 12,251,241 B2
(45) Date of Patent: Mar. 18, 2025

(54) HEALTH MANAGEMENT DEVICE FOR MOTHER AND FETUS

(71) Applicant: Diane A. Geer, Nashville, TN (US)

(72) Inventor: Diane A. Geer, Nashville, TN (US)

( * ) Notice: Subject to any disclaimer, the term of this patent is extended or adjusted under 35 U.S.C. 154(b) by 43 days.

(21) Appl. No.: 18/296,769

(22) Filed: Apr. 6, 2023

(65) Prior Publication Data

US 2024/0335172 A1    Oct. 10, 2024

(51) Int. Cl.
*A61B 5/00* (2006.01)
*A61B 5/11* (2006.01)
*A61M 5/00* (2006.01)

(52) U.S. Cl.
CPC ............ *A61B 5/746* (2013.01); *A61B 5/1107* (2013.01); *A61B 5/4356* (2013.01); *A61B 5/6802* (2013.01); *A61B 5/6833* (2013.01); *A61B 5/742* (2013.01); *A61M 5/00* (2013.01)

(58) Field of Classification Search
CPC ..... A61B 5/746; A61B 5/1107; A61B 5/4356; A61B 5/6802; A61B 5/6833; A61B 5/742; A61M 5/00
See application file for complete search history.

(56) References Cited

U.S. PATENT DOCUMENTS

| | | | |
|---|---|---|---|
| 2006/0204532 A1* | 9/2006 | John | A61M 5/16809 424/422 |
| 2017/0089887 A1* | 3/2017 | Souza | G06T 7/0016 |
| 2018/0353142 A1* | 12/2018 | Shah | A61B 5/0022 |
| 2019/0038236 A1* | 2/2019 | Hays | G06F 3/167 |

* cited by examiner

*Primary Examiner* — Brian A Zimmerman
*Assistant Examiner* — Cal J Eustaquio
(74) *Attorney, Agent, or Firm* — Briggs IP; Jeremy A. Briggs

(57) ABSTRACT

A health management device for a user is described. The device may include a flexible body having an interior surface and an exterior surface. The interior surface may be configured to be adhered to a user skin. The device may further include a sensor attached to the interior surface. The sensor may be configured to measure user biometric information. Further, the device may include a processor configured to determine a user contraction level based on the user biometric information. The processor may additionally determine that the user contraction level is greater than a first threshold. The processor may perform a predefined action responsive to a determination that the user contraction level is greater than the first threshold. The predefined action may include causing a pharmaceutical disbursement unit to disburse a predefined quantity of medicine into the user skin.

13 Claims, 5 Drawing Sheets

HEALTH MANAGEMENT DEVICE FOR MOTHER AND FETUS

TECHNICAL FIELD

The present disclosure relates to a health management device for mother and fetus, and more particularly, to a health management device that continuously monitors and wirelessly transmits biometric information of mother and fetus to a cloud storage for attention of medical staff.

BACKGROUND

A mother in active labor may require continuous monitoring to safeguard health of the mother and ensure delivery of healthy baby. A conventional health management system monitors mother and fetus health by using wired sensors that may be hooked (or attached) to mother's body. The sensors may measure vital biometric information of mother and fetus, and medical staff may assist the mother based on the measured biometric information.

While the conventional system may provide benefits to the mother and the medical staff, the wired sensors are typically bulky and the process of hooking and unhooking the sensors may be cumbersome. For example, when the mother needs to use restroom or desires to walk, the medical staff may be required to unhook the sensors. Further, the medical staff may hook the sensors again when the mother returns. This process of hooking and unhooking the sensors may cause inconvenience to the mother and the medical staff. Further, the system may not capture vital biometric information of the mother and the fetus when the sensors are not hooked to the mother. The loss of biometric information may result in medical complications.

Furthermore, the conventional system is typically installed in a medical facility. Therefore, the mother needs to be physically present in the medical facility for the medical staff to monitor the biometric information. The conventional system may not work when the mother is in a home set-up.

Thus, there exists a need for a health management system and method that may enable continuous monitoring of biometric information of mother and fetus, in a medical facility as well as in a home set-up.

It is with respect to these and other considerations that the disclosure made herein is presented.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
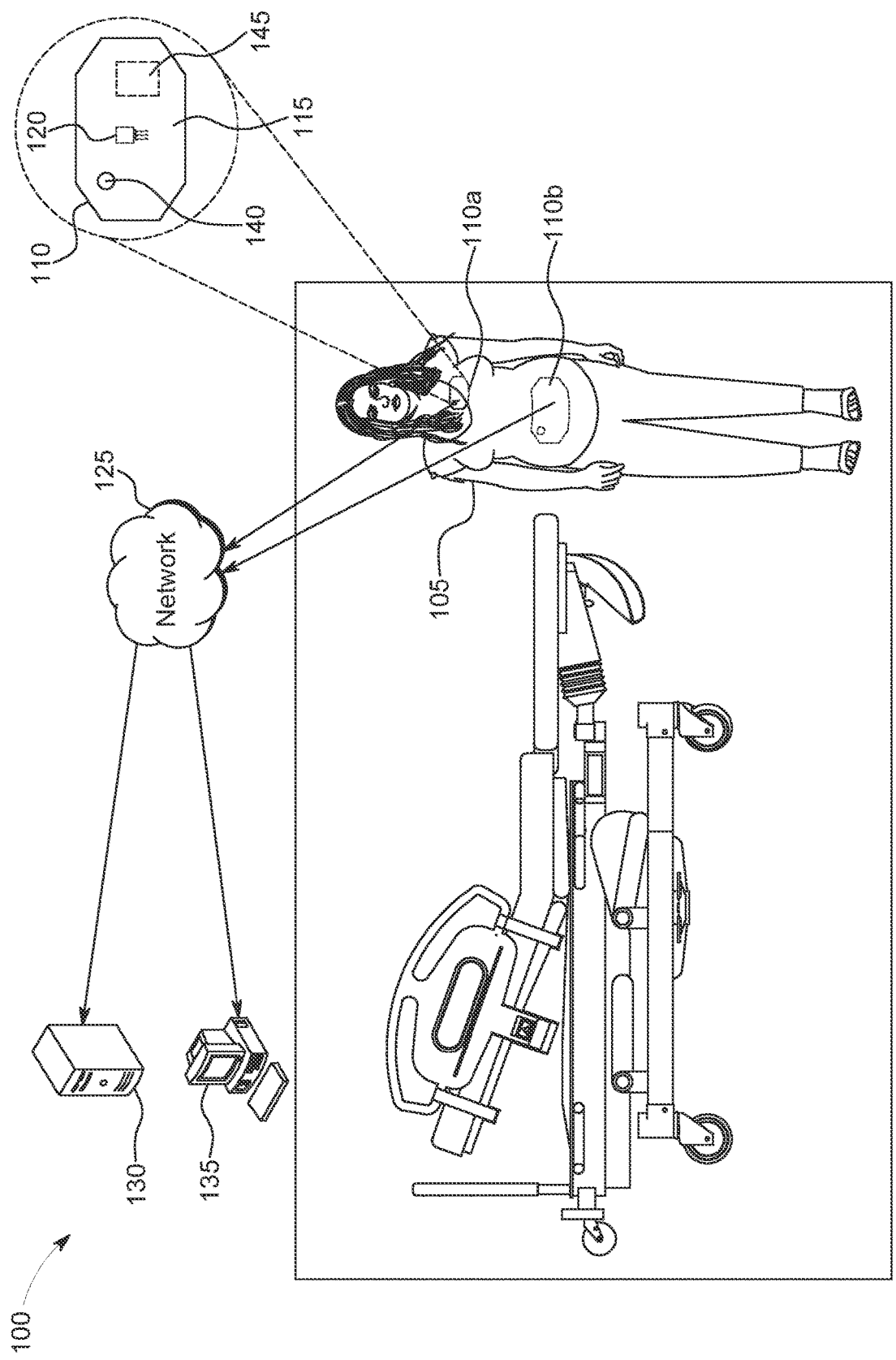
FIG. 1 depicts an example environment in which techniques and structures for providing the systems and methods disclosed herein may be implemented.

The present disclosure describes a health management device that may measure biometric information of a user in real-time. The user may be a mother in active labor. The device may be a flexible patch that may adhere to the mother's skin. For example, the device may be adhered to mother skin on a left chest region (e.g., in proximity to the heart) and/or to the mother skin around the abdominal region. The device may include sensors that may measure real-time biometric information of the mother and the fetus. The device may wirelessly transmit the measured biometric information to a remote server or a medical staff user device, so that medical staff can attend to the mother in case the biometric information indicates an actionable medical condition. The remote server or the medical staff user device may further store the received biometric information in local memory or a cloud storage, thus ensuring that no vital health related information associated with the mother or the fetus is lost.

In some aspects, two devices may be adhered to the mother skin. A first device may be adhered to the left chest region and a second device may be adhered to the abdominal region. The first device may capture biometric information, e.g., heart rate, of the mother. The second device may capture biometric information of the mother and the fetus. For example, the second device may measure mother contraction intensity, and fetus heart rate.

In some aspects, the device may include a flexible body having an interior surface and an exterior surface. The interior surface may adhere to the mother skin. Further, the interior surface may include the sensors that measure mother and fetus biometric information. The exterior surface may include a visual indication portion on which the medical staff may removably attach a visual indicator indicating a pre-existing mother medical condition. For example, the visual indicator may be a color-coded sticker, and different colors may indicate different pre-existing medical conditions. The visual indicator may assist different medical staff members who may attend the mother to quickly recognize mother's pre-existing medical conditions, and provide medications accordingly.

The device may further include a pharmaceutical disbursement unit that may disburse a preset quantity of medicines (e.g., anesthetics) into the mother skin. The device may be configured to control medicine disbursement dosage into the mother skin based on mother biometric information. For example, the device may be configured to determine mother contraction level based on the mother biometric information, and may control dosage of medicine disbursement from the pharmaceutical disbursement unit based on the determined mother contraction level.

The present disclosure discloses a health management device that may be removably adhered to the mother skin. The device may wirelessly transmit real-time biometric information of the mother and the fetus to a remote system or user device, thus the information is not lost. Specifically, since the information is not passed from one medical staff to another in the form of handwritten notes, probability of information loss is considerably reduced. Further, since the device wirelessly transmits the biometric information, no wired connections are required between the device and the remote system/user device. Therefore, the mother can conveniently move, e.g., walk or go to the restroom, without risking loss of biometric information transmission. Furthermore, the device includes a pharmaceutical disbursement unit that may automatically disburse vital medicines, e.g., anesthetics, into the mother skin based on mother's contraction level, thus assisting the mother in alleviating pain associated with the contractions.

These and other advantages of the present disclosure are provided in detail herein.

Illustrative Embodiments

The disclosure will be described more fully hereinafter with reference to the accompanying drawings, in which example embodiments of the disclosure are shown, and not intended to be limiting.

FIG. 1 depicts an example environment 100 in which techniques and structures for providing the systems and methods disclosed herein may be implemented. The environment 100 may include a user 105 who may be located in a medical facility (e.g., a hospital) or a home set-up. The user 105 may be a mother who may be in active labor. Hereinafter, the user 105 is referred to as the mother 105.

The mother 105 may have one or more health management devices 110a, 110b (or devices 110) adhered to mother body or skin. For example, the device 110a may be adhered to the mother skin around the chest region (e.g., a left-side chest region, in proximity to the heart), and the device 110b may be adhered to the mother skin around the abdominal region (e.g., in proximity to fetus position). The device 110a and the device 110b may be similar to each other, however, in some aspects, the device 110a may have shorter dimensions relative to device 110b dimensions. For example, the device 110a may have a length in a range of 3-5 inches, and breadth in a range of 2-3 inches. On the other hand, the device 110b may have a length in a range of 10-12 inches, and breadth in a range of 5-7 inches. In other aspects (not shown), the device 110a and the device 110b may have same or equivalent dimensions.

The device 110 may have a flexible body having a high flexibility coefficient so that the device 110 may be adhered to users (e.g., mothers) of different physiologies. In an exemplary aspect, the flexible body may be a patch that may be formed from woven cotton, rayon fabric, sterile polyurethane, and/or other similar material that may be conveniently and safely adhered to the mother skin. In additional aspects, the flexible body may have anti-bacterial properties, which may protect the mother 105 from bacterial infections.

The flexible body may have an interior surface (not shown) and an exterior surface 115. The interior surface may include an adhesive material that may enable the interior surface (and hence the device 110) to be adhered to the mother skin. The adhesive material may be any medical grade adhesive including, but not limited to, epoxy or acrylate based adhesive or medical grade silicon.

In some aspects, the interior surface (or the device 110) may be adhered to the mother skin by using a belt or a band (not shown), in addition to or alternative to adhering by using the adhesive material. The belt or the band may provide additional stability and adhesion, which may enable the device 110 to securely adhere to the mother skin. The belt or the band may specifically be used for mothers with relatively larger physiologies (e.g., overweight mothers).

The device 110 may be securely adhered to the mother skin, by using interior surface adhesive material and/or the belt/band, such that the device 110 may not move relative to mother skin or get unhooked (or "come off") when the mother 105 moves. For example, the device 110 may be adhered to the mother skin such that the device 110 may not get unhooked when the mother 105 goes a walk or to the restroom.

The interior surface may further include one or more sensors 120 that may be adhered to the mother skin when the interior surface is adhered. The sensors 120 may be configured to measure biometric information associated with the mother 105 and the fetus inside mother womb. The sensors 120 may be wet electrode sensors, dry electrode sensors, textile-based sensors, knitted integrated sensors (KIS), and/or the like. Examples of the sensors 120 include, but are not limited to, heart rate sensors, contraction intensity sensors, pulse rate sensors, oxygen level sensors, blood pressure sensors, sonogram or ultrasound based cameras, and/or the like.

In an exemplary aspect, sensors associated with the device 110a may measure heart rate and other vital biometric information of the mother 105. The device 110b may measure fetus heart rate, and other vital biometric information of both the mother 105 and the fetus in the mother womb.

Examples of the biometric information measured by the sensors 120 include, but are not limited to, mother contraction intensity, mother heart rate, mother oxygen level, mother labor activity, fetus heart rate, fetal visual and/or audio feed, and/or the like. The mother labor activity may include information associated with whether the mother 105 is pushing or not. Further, the sensors 120 may measure the mother contraction intensity by measuring density or stiffness of underlying skin muscles on which the device 110 may be adhered. A person ordinarily skilled in the art may appreciate that stiff skin muscles may indicate contraction. Furthermore, an elevated heart rate may indicate contraction. In some aspects, the sensors 120 may capture both the heart rate and skin stiffness to measure the mother contraction intensity.

In additional aspects, the sensors 120 may capture fetus images in the mother womb by using the sonogram or ultrasound based cameras. The sensors 120 may additionally include a microphone that may capture fetus audio feed. For example, the microphone may capture fetus heartbeat.

The device 110 may be wirelessly connected with external devices via a network 125, and may transmit real-time biometric information measured by the sensors 120 to one or more external devices. The network 125 may be, for example, a communication infrastructure in which the connected devices discussed in various embodiments of this disclosure may communicate. The network 125 may be and/or include the Internet, a private network, public network or other configuration that operates using any one or more known communication protocols such as, for example, transmission control protocol/Internet protocol (TCP/IP), Bluetooth®, BLE®, Wi-Fi based on the Institute of Electrical and Electronics Engineers (IEEE) standard 802.11, UWB, and cellular technologies such as Time Division Multiple Access (TDMA), Code Division Multiple Access (CDMA), High Speed Packet Access (HSPDA), Long-Term Evolution (LTE), Global System for Mobile Communications (GSM), and Fifth Generation (5G), to name a few examples.

The external devices may include, for example, a central medical facility server 130, a medical staff user device 135, and/or the like. The medical staff user device 135 may be a computer, a laptop, a tablet, a mobile phone, or other similar device having communication capabilities, associated with a doctor or a nurse who may assist the mother 105. For example, the doctor or the nurse may assist the mother 105 when the mother or fetus heart rate decreases or increases beyond a threshold level, or when the mother 105 experiences high contraction intensity. A person ordinarily skilled in the art may appreciate that pain experienced by the mother 105 may directly correlate with the contraction intensity. Therefore, the mother 105 may require assistance from the doctor or the nurse when the contraction intensity (and hence pain) increases above a threshold level.

In some aspects, the doctor or the nurse may access the biometric information transmitted by the device 110 on the medical staff user device 135 (or the central medical facility server 130) by logging into a device application ("app") that may be installed on the medical staff user device 135. By logging into the app, the doctor or the nurse may monitor the real-time biometric information that may be wirelessly transmitted by the device 110, and may assist the mother 105 when the mother 105 or the fetus may require attention.

In some aspects (not shown), more than one device 110b may be adhered to the mother skin around the abdominal region, if the mother 105 may be expecting twins, triplets, etc. For example, if the mother 105 may be expected twins, two devices (e.g., the device 110b) may be adhered to the mother skin around the abdominal region to separately capture biometric information of each fetus. In this case, one patch (e.g., a first patch) may capture first baby's heart rate and overall uterine contractions and another patch (e.g., a second patch) may capture second baby's heart rate. Further, in this case, the doctor or the nurse may access biometric information of each fetus separately on the app (e.g., by using uniquely identifiable serial number associated with each patch), and hence check health status of each fetus.

Since the device 110 transmits the mother 105 and fetus biometric information in real-time to the external devices described above, probability of information loss is considerably reduced. For example, the central medical facility server 130 and/or the medical staff user device 135 may store the biometric information in respective device memory, and hence the information may not be lost.

Further, since the device 110 is adhered to the mother skin and the device 110 wirelessly transmits the biometric information, information transmission is not lost when the mother 105 moves. For example, the device 110 may keep on continuously transmitting (i.e., transmitting at a predefined frequency) the biometric information to the central medical facility server 130 and/or the medical staff user device 135 even when the mother 105 is out of her bed, and goes to the restroom or for a walk.

Furthermore, even if the mother 105 is in a home set-up, the mother 105 may adhere the device 110 to her skin, and the device 110 may wirelessly transmit the biometric information to the central medical facility server 130 and/or the medical staff user device 135. Therefore, by using the device 110, the mother 105 may not be required to be physically present in the medical facility to get medical assistance. In this case, the doctor or the nurse may monitor the mother 105 and fetus health condition remotely via the received biometric information. Further, the doctor or the nurse may send a notification to the mother 105 (via the app installed on a mother user device, not shown) or send an ambulance to mother home, if the doctor or the nurse determine that the mother 105 may require admission to the medical facility, based on the biometric information. Home births are usually assisted by midwives. In this case, the doctor or the nurse may support the midwife during home birth, by getting real-time mother and fetus health condition status and transmitting real-time support to the midwife. In this manner, the present disclosure may assist in eliminating home birthing errors.

The device 110 may also transmit the biometric information, e.g., the fetus images or the fetus heartbeat, via the app, to the mother user device or a user device associated with family member(s), who may desire to record the biometric information as a souvenir. In some aspects, the app may provide limited access to the biometric information to the user device associated with the family member(s) or the mother user device, to ensure data confidentiality.

The device 110 (specifically the exterior surface 115) may additionally include a visual indication portion configured to receive a visual indicator 140 indicating mother's pre-existing health condition. The visual indicator 140 may be a colored indicator, e.g., a sticker or a blunt-ended pin, which may be pasted on the exterior surface 115. In an exemplary aspect, different colored indicators may indicate different pre-existing mother medical condition. For example, a red colored indicator may indicate pre-existing inflections (e.g., vaginal infection) that the mother 105 may have, a yellow colored indicator may indicate pre-term labor, an orange colored indicator may indicate complications related to the fetus, or high blood pressure, diabetes, bleeding, etc. associated with the mother 105, and/or the like.

A portion of the exterior surface 115 (e.g., the visual indication portion) may include an adhesive substrate (e.g., reusable stickers or Velcro™), on which the visual indicator 140 may be pasted.

Presence of the visual indication portion and the visual indicator 140 may assist the medical staff who may attend the mother 105. A person ordinarily skilled in the art may appreciate that for certain pre-existing medical conditions, e.g., vaginal infection, the mother 105 may require specific medicines at a predefined frequency when the mother 105 is in labor, to ensure that the baby is not affected by the infection. Visual indicator 140 presence (e.g., a red colored indicator) on the exterior surface 115 may act as a "reminder" for the nurse(s) who may assist the mother 105 to provide the specific medicine to the mother 105 on time. In addition, since the visual indicator 140 is pasted on the exterior surface 115, information regarding the pre-existing mother medical condition is not lost when the nurses change shifts. Therefore, the new nurse may also provide timely medicine to the mother 105, when the nurses' shifts change.

The device 110 may additionally include a pharmaceutical disbursement unit 145 that may be attached to the interior surface. Specifically, the pharmaceutical disbursement unit 145 may also adhere to the mother skin, when the interior surface is adhered to the mother 105. The pharmaceutical disbursement unit 145 may be configured to disburse a predefined quantity of medicine into the mother skin. A person ordinarily skilled in the art may appreciate that mothers may require specific medicines, e.g., anesthetics, to get relief from pain, specifically during contractions. In an exemplary aspect, the pharmaceutical disbursement unit 145 may be configured to disburse a predefined quantity of anesthetics into the mother's skin, to provide relief to the mother 105 when the mother 105 experiences contractions. The process of disbursement of medicines into the mother's skin may be understood in detail in conjunction with FIG. 3.

In additional aspects, the device 110 may include a fingerprint identification unit (not shown) disposed at one or more edges of the device 110. A nurse may place a finger on the fingerprint identification unit to record her presence in proximity to the device 110. Stated another way, by placing the finger on the fingerprint identification unit, the nurse may indicate that the nurse has attended to the mother 105. The device 110 may send information associated with the fingerprint (e.g., date and time when the nurse placed the finger on the fingerprint identification unit, unique identifier associated with the nurse, etc.) to the central medical facility server 130 for record purposes.

The device 110, as described in the present disclosure, is washable and re-usable. For example, the mother 105 may wash the device 110 and may re-adhere the device 110 to the skin after washing. Furthermore, the device 110 may be customizable based on mother's requirements. An example embodiment of a customized device 110 is depicted in FIG. 2.

Figure 2:
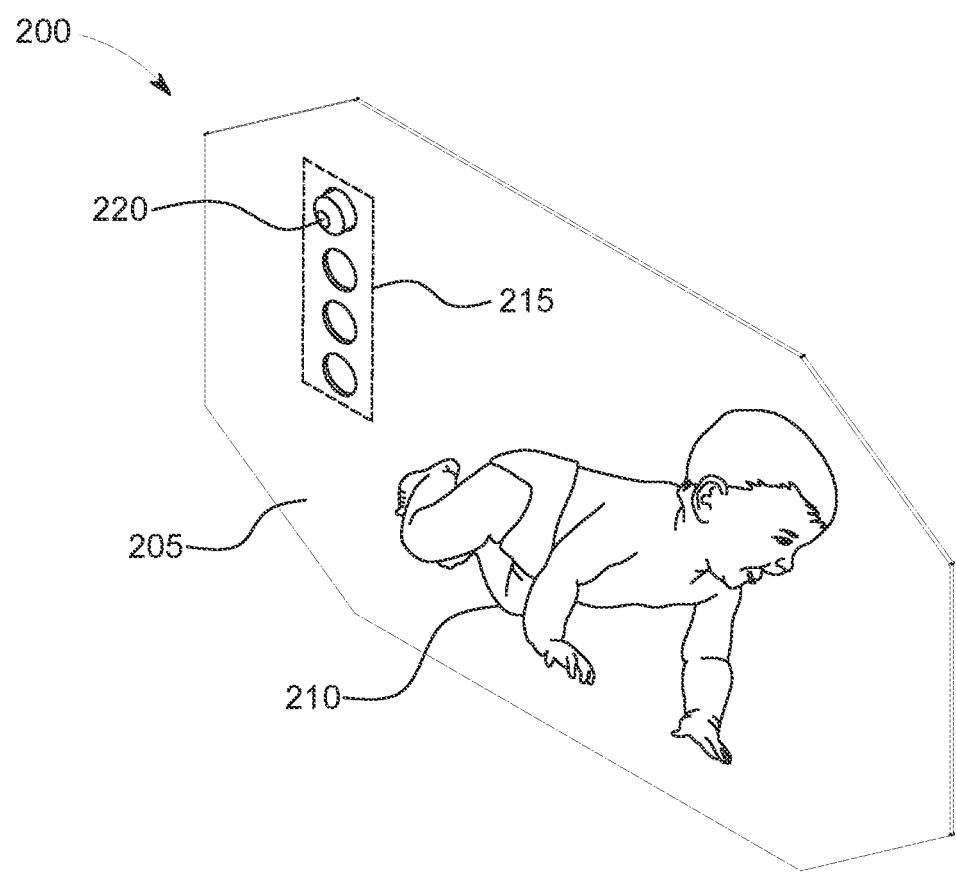
FIG. 2 depicts a snapshot of an example exterior surface of a health management device, in accordance with the present disclosure.

FIG. 2 depicts a snapshot of an example exterior surface 205 of a health management device 200, in accordance with the present disclosure. The device 200 may be same as the device 110, and the exterior surface 205 may be similar to the exterior surface 115.

The exterior surface 205 may be customizable. For example, the exterior surface 205 may include a picture of a baby boy 210 if the mother 105 expects a baby boy. On the other hand, the exterior surface 205 may include a picture of a baby girl if the mother 105 expects a baby girl. Similarly, the exterior surface 205 may be colored according to baby gender, e.g., blue color for baby boy, pink color for baby girl, and yellow color if the gender is unknown.

In further aspects, the exterior surface 205 may include a visual indication portion 215 that may include one or more fastening means, e.g., holes. A visual indicator 220, which may be a color coded blunt-ended pin, may be inserted into a hole. The visual indicator 220 may be same as the visual indicator 140, and may be used to indicate the pre-existing mother medical condition.

Exterior surface snapshot depicted in FIG. 2 is exemplary, and should not be construed as limiting the present disclosure scope. Further structural changes may be made to the exterior surface 205, without departing from the present disclosure scope.

Figure 3:
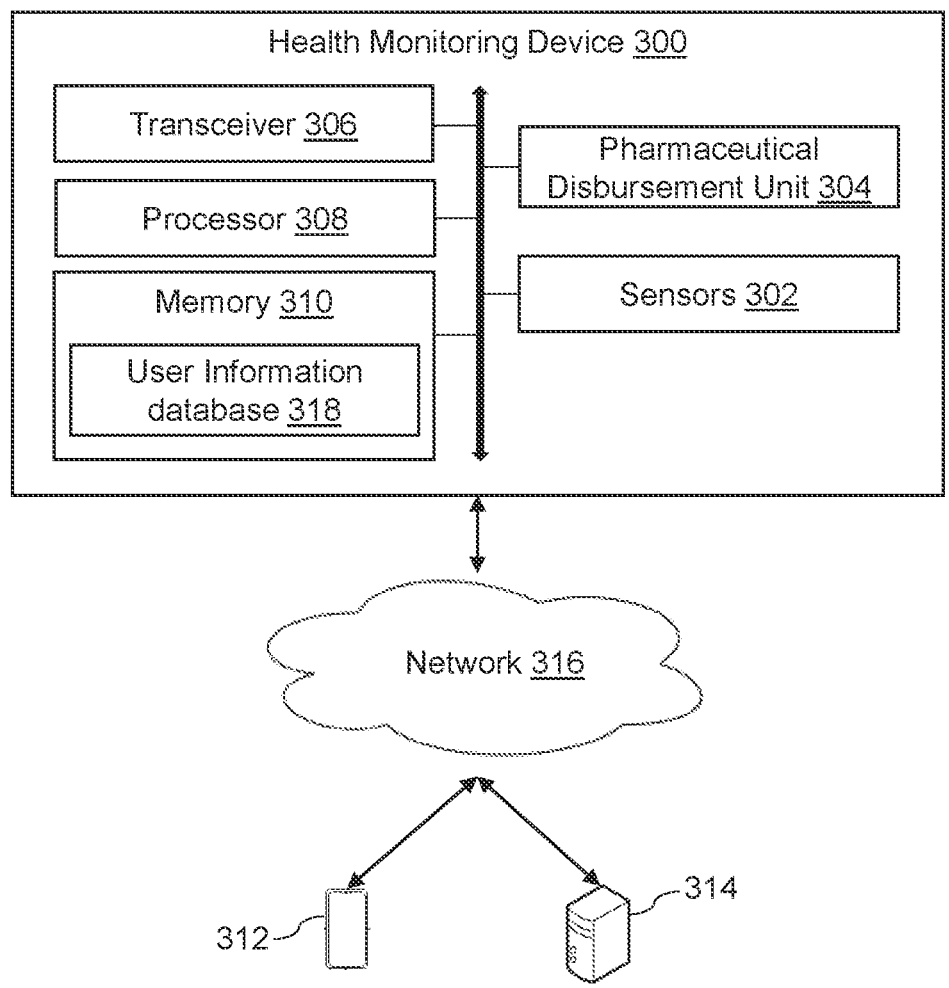
FIG. 3 depicts a block diagram of an example health management device in accordance with the present disclosure.

FIG. 3 depicts a block diagram of an example health management device 300 in accordance with the present disclosure. While describing FIG. 3, reference may be made to FIG. 4. The device 300 may be same as the device 110, and may be adhered to mother skin. The device 300 may include one or more sensors 302 and a pharmaceutical disbursement unit 304. The sensors 302 may be same as the sensors 120, and may be configured to measure biometric information of the mother 105 and the fetus. Further, the pharmaceutical disbursement unit 304 may be same as the pharmaceutical disbursement unit 145, and may be configured to disburse specific medicines, e.g., anesthetics, into the mother skin.

The device 300 may further include a transceiver 306, a processor 308, and a memory 310. The transceiver 306, the processor 308, the memory 310, the sensors 120 and the pharmaceutical disbursement unit 304 may be communicatively connected with each other via a bus.

The transceiver 306 may be configured to receive and transmit information from/to internal and external components or devices. For example, the transceiver 306 may be configured to receive real-time biometric information from the sensors 302, and may wirelessly transmit the biometric information to a user device 312 and/or a server 314, via a network 316. The user device 312 may be same as the medical staff user device 135, the server 314 may be same as the central medical facility server 130, and the network 316 may be same as the network 125.

As described in conjunction with FIG. 1, the medical staff attending the mother 105 may view the real-time biometric information on the user device 312 or the server 314 (by accessing the app that may be installed on the device/server), and may perform one or more actions based on the biometric information. For example, the medical staff may provide medicines or assistance to the mother 105 when the mother or the fetus heart rate fluctuates above a threshold level, or may recommend the mother 105 not to push during contraction if the biometric information indicates that the mother 105 may be pushing.

In addition to transmitting the biometric information to the user device 312 and/or the server 314, the transceiver 306 may send the biometric information to the memory 310 for storage purpose. Specifically, the memory 310 may include a user information database 318 that may store the mother and fetus biometric information received from the transceiver 306.

In some aspects, the memory 310 may store programs in code and/or store data for performing various device 300 operations in accordance with the present disclosure. Specifically, the processor 308 may be configured and/or programmed to execute computer-executable instructions stored in the memory 310 for performing various device 300 functions in accordance with the disclosure. Consequently, the memory 310 may be used for storing code and/or data code and/or data for performing operations in accordance with the present disclosure.

In one or more aspects, the processor 308 may be disposed in communication with one or more memory devices (e.g., the memory 310 and/or one or more external databases (not shown in FIG. 3)). The memory 310 can include any one or a combination of volatile memory elements (e.g., dynamic random-access memory (DRAM), synchronous dynamic random access memory (SDRAM), etc.) and can include any one or more nonvolatile memory elements (e.g., erasable programmable read-only memory (EPROM), flash memory, electronically erasable programmable read-only memory (EEPROM), programmable read-only memory (PROM), etc.).

The memory 310 may be one example of a non-transitory computer-readable medium and may be used to store programs in code and/or to store data for performing various operations in accordance with the disclosure. The instructions in the memory 310 can include one or more separate programs, each of which can include an ordered listing of computer-executable instructions for implementing logical functions.

In operation, the processor 308 may obtain the biometric information of the mother 105 and fetus from the user information database 318, and determine mother contraction level based on the biometric information. Specifically, as described in conjunction with FIG. 1, the biometric information may include mother contraction intensity. The processor 308 may use the mother contraction intensity measured over a time duration (e.g., over 15 or 30 minutes), and determine duration of each contraction and frequency of contraction that the mother 105 may have experienced over the time duration. For example, the processor 308 may determine that the mother 105 may have experienced two contractions of "high" intensity for one minute each in last 30 minutes, or may have experienced one contraction of "low" intensity for one minute in the last 30 minutes, based on mother contraction intensity obtained from the user information database 318. In some aspects, the processor 308 may determine the level of contraction, e.g., "high" or "low", by comparing the obtained contraction intensity with a predefined threshold.

Responsive to obtaining the contraction intensity and determining contraction frequency and duration, the processor 308 may determine the contraction level. For example, the processor 308 may assign a contraction rating or rank (e.g., on a scale of 1 to 10) to the mother 105, based on the contraction intensity, duration and frequency information. The contraction rating or rank may denote the contraction level. As an example, the processor 308 may assign a contraction level of 8 to the mother 105 if the mother 105 experiences more than two "high" intensity contractions in 15 minutes, and may assign a contraction level of 4 if the mother 105 experiences less than one "high" intensity contraction in 2 hours. In some aspects, a matrix or rule-set associated with multiple contraction levels with respect to contraction intensity, frequency and duration may be pre-stored in the memory 310, and the processor 308 may use the matrix to assign the contraction level to the mother 105.

In addition to determining the mother contraction level, the processor 308 may determine additional fetus related information. For example, the processor 308 may determine nuchal cord or breech position based on the fetus images captured by the sensors 302 (that may be part of the biometric information stored in the user information database 318).

Responsive to determining the contraction frequency and duration, and fetus related information, the processor 308 may send the information to the transceiver 306, which may transmit the information to the user device 312 and/or the server 314, and the medical staff may view the information.

Figure 4:
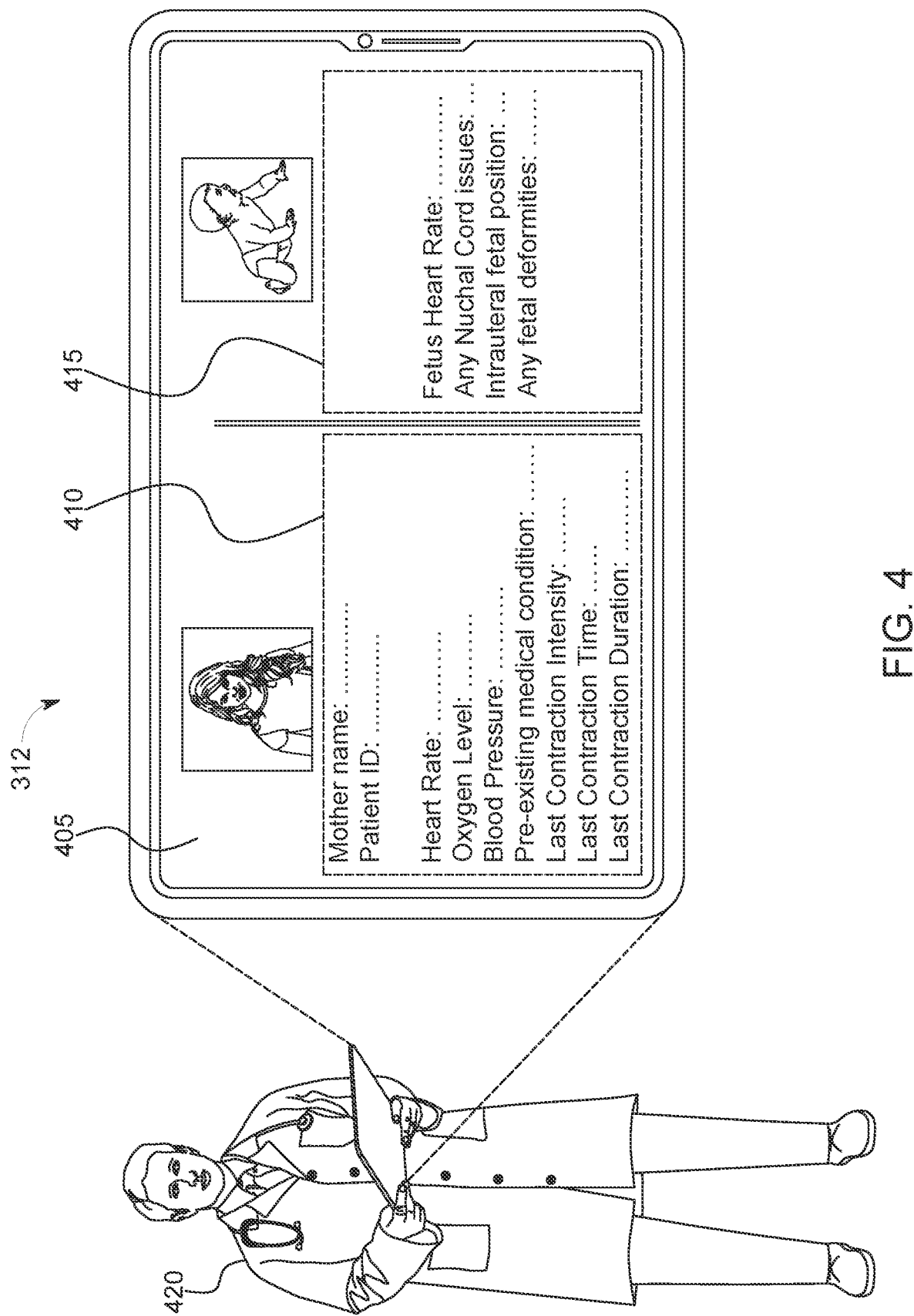
FIG. 4 depicts an example snapshot of a display screen displaying mother and fetus biometric information in accordance with the present disclosure.

An example snapshot of a view on the user device 312 is depicted in FIG. 4. Specifically, FIG. 4 depicts an example snapshot of a display screen 405 displaying mother and fetus biometric information on the user device 312 in accordance with the present disclosure. As shown in views 410 and 415, the biometric information associated with the mother 105 may be displayed separately from the biometric information associated with the fetus on the display screen 405. Medical staff member 420 may analyze the biometric information, and may perform one or more actions based on the biometric information.

The processor 308 may be further configured to determine whether the determined mother contraction level is greater than a first predefined threshold (that may be pre-stored in the memory 310). Specifically, responsive to determining the mother contraction level (e.g., 6), the processor 308 may fetch the first predefined threshold (e.g., 4) from the memory 310, and compare the determined mother contraction level with the first threshold level. The processor 308 may transmit, via the transceiver 306, a first activation signal to the pharmaceutical disbursement unit 304 when the processor 308 determines that the mother contraction level is greater than the first threshold level.

Responsive to receiving the first activation signal, the pharmaceutical disbursement unit 304 may disburse a first predefined quantity of medicine (e.g., anesthetics) into the mother skin. In some aspects, the first activation signal may include instructions for medicine disbursement, including the first predefined quantity, and the pharmaceutical disbursement unit 304 may disburse the medicine into the mother skin according to the received instructions.

In some aspects, the processor 308 may transmit the first activation signal one time when the processor 308 determines that the mother contraction level may be greater than the first threshold value. In other aspects, the processor 308 may transmit more than one first activation signals at a predefined frequency, when (or after) the processor 308 determines that the mother contraction level may be greater than the first threshold value. For example, the processor 308 may transmit the first activation signals every 30 minutes to the pharmaceutical disbursement unit 304, when the mother contraction level increases above the first threshold value even once. In this case, the pharmaceutical disbursement unit 304 may disburse the medicine into the mother skin every 30 minutes, thus providing continuous relief to the mother 105 from the pain that she may be experiencing due to contractions.

The processor 308 may be further configured to compare the determined mother contraction level with a second predefined threshold (that may be pre-stored in the memory 310), and determine whether the mother contraction level is greater than the second predefined threshold. In some aspects, the second predefined threshold may be greater than the first predefined threshold. For example, the first predefined threshold may be 4, and the second predefined threshold may be 8. Responsive to determining that the mother contraction level may be greater than 8 (i.e., the second predefined threshold), the processor 308 may transmit, via the transceiver 306, a notification to the user device 312 and/or the server 314. The notification may indicate that the mother 105 may be experiencing higher level of pain, as the contraction level may be greater than the second predefined threshold.

The medical staff member 420 may view the notification on the display screen 405, and transmit one or more inputs to the transceiver 306. In some aspects, the inputs may be associated with instructions to increase medicine dose to the mother 105. The transceiver 306 may receive the inputs from the user device 312 and/or the server 314, and send the received inputs to the processor 308. Responsive to obtaining the inputs, the processor 308 may transmit a second activation signal to the pharmaceutical disbursement unit 304. The pharmaceutical disbursement unit 304 may disburse a second predefined quantity of medicine into the mother skin, responsive to receiving the second activation signal. The second predefined quantity may be greater than the first predefined quantity.

Although the description above describes an aspect where the medical staff member 420 provides the input to increase the medicine dose to the mother 105, in some aspects, the processor 308 may automatically increase the medicine dose to the mother 105, responsive to determining that the mother contraction level may be greater than the second predefined threshold. In this case, the processor 308 may directly send the second activation signal to the pharmaceutical disbursement unit 304, without waiting for medical staff member input. In yet another aspect, the medical staff member 420 may obtain mother 105 consent before transmitting the input to the processor 308 to increase the medical dose.

By increasing the medical dose, the device 300 may assist the mother 105 in alleviating the pain that the mother 105 may be experiencing due to greater contraction level. Further, since the processor 308 automatically detects that the contraction level may be greater than the second predefined threshold and transmits the notification to the medical staff member 420, probability of human error in information transmission or delay in manual transmission of information may be greatly reduced.

Although the description above is described by using a human mother as an example, the device 300 may be used for any mammal, e.g., animals as well.

Figure 5:
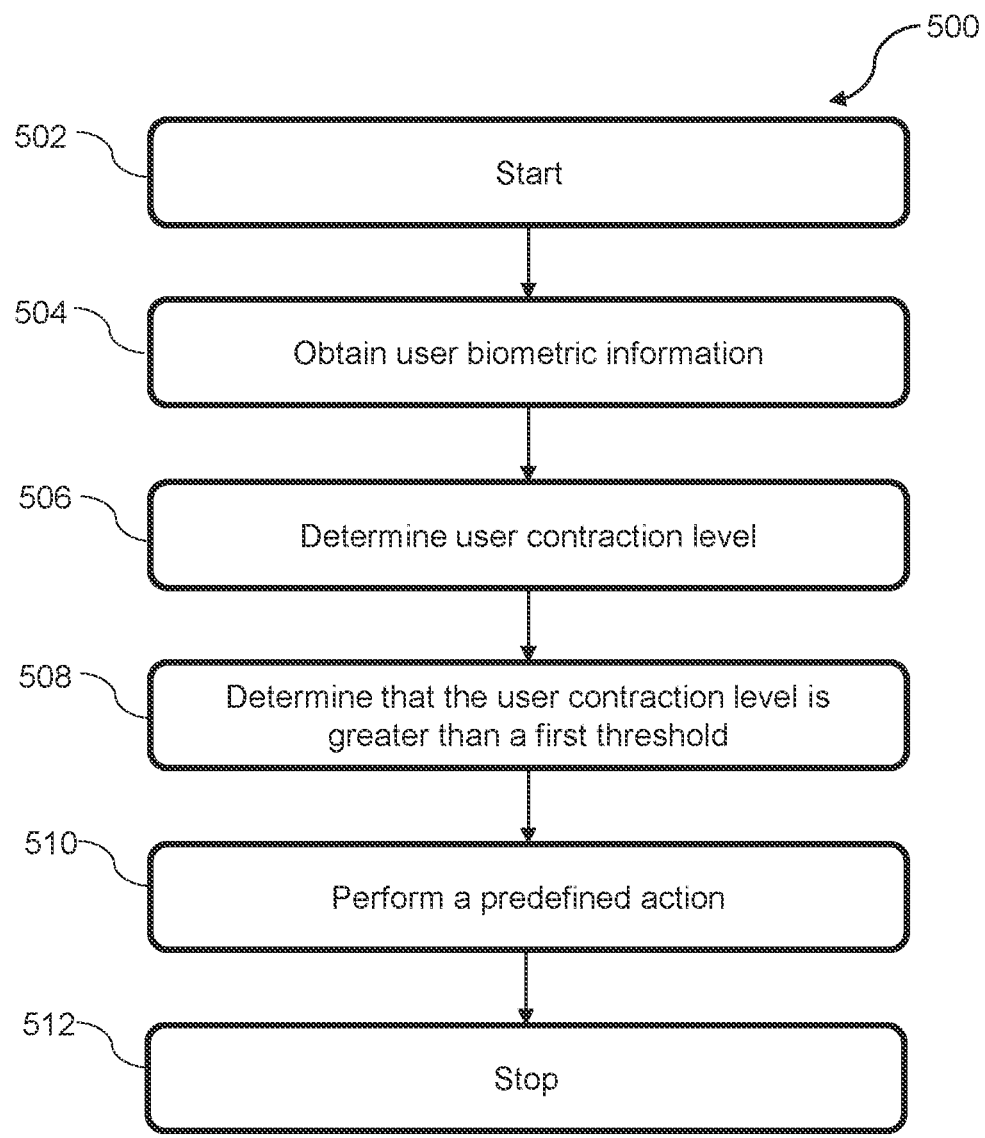
FIG. 5 depicts a flow diagram of an example health management method in accordance with the present disclosure.

FIG. 5 depicts a flow diagram of an example health management method 500 in accordance with the present disclosure. FIG. 5 may be described with continued reference to prior figures, including FIGS. 1-4. The following process is exemplary and not confined to the steps described hereafter. Moreover, alternative embodiments may include more or less steps that are shown or described herein and may include these steps in a different order than the order described in the following example embodiments.

Referring to FIG. 5, at step 502, the method 500 may commence. At step 504, the method 500 may include obtaining, by the processor 308, biometric information associated with the mother 105 from the sensors 302. At step 506, the method 500 may include determining, by the processor 308, the mother contraction level based on the obtained biometric information, as described in conjunction with FIG. 3.

At step 508, the method 500 may include determining, by the processor 308, that the mother contraction level is greater than the first threshold. At step 510, the method 500 may include performing, by the processor 308, a predefined action responsive to the determination at the step 508 that the mother contraction level is greater than the first threshold. As described in conjunction with FIG. 3, the predefined action may include transmitting the first activation signal to the pharmaceutical disbursement unit 304. The pharmaceutical disbursement unit 304 may disburse the first predefined quantity of medicine into the mother skin, responsive to receiving the first activation signal.

At step 512, the method 500 may stop.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a feature, structure, or characteristic is described in connection with an embodiment, one skilled in the art will recognize such feature, structure, or characteristic in connection with other embodiments whether or not explicitly described.

Further, where appropriate, the functions described herein can be performed in one or more of hardware, software, firmware, digital components, or analog components. For example, one or more application specific integrated circuits (ASICs) can be programmed to carry out one or more of the systems and procedures described herein. Certain terms are used throughout the description and claims refer to particular system components. As one skilled in the art will appreciate, components may be referred to by different names. This document does not intend to distinguish between components that differ in name, but not function.

It should also be understood that the word "example" as used herein is intended to be non-exclusionary and non-limiting in nature. More particularly, the word "example" as used herein indicates one among several examples, and it should be understood that no undue emphasis or preference is being directed to the particular example being described.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Computing devices may include computer-executable instructions, where the instructions may be executable by one or more computing devices such as those listed above and stored on a computer-readable medium.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating various embodiments and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A health management device for a user comprising:
a flexible body having an interior surface and an exterior surface, wherein the interior surface is configured to be adhered to user skin;
a sensor disposed at the interior surface, wherein the sensor is configured to measure user biometric information;
a pharmaceutical disbursement unit configured to disburse a medicine in the user skin; and
a processor configured to:
obtain the user biometric information from the sensor;

determine a user contraction level based on the user biometric information;

determine that the user contraction level is greater than a first threshold;

transmit a first activation signal to the pharmaceutical disbursement unit responsive to a determination that the user contraction level is greater than the first threshold, wherein the pharmaceutical disbursement unit disburses a first predefined quantity of medicine in the user skin responsive to receiving the first activation signal;

determine that the user contraction level is greater than a second threshold;

transmit a notification to an external device responsive to a determination that the user contraction level is greater than the second threshold;

obtain an input from the external device responsive to transmitting the notification; and transmit a second activation signal to the pharmaceutical disbursement unit responsive to obtaining the input, wherein the pharmaceutical disbursement unit disburses a second predefined quantity of medicine in the user skin responsive to receiving the second activation signal.

2. The health management device of claim 1, wherein the user biometric information comprises at least one of: a user contraction intensity, a user heart rate, a user oxygen level, a user labor activity, a fetus heart rate, fetus visual and/or audio feed.

3. The health management device of claim 1 further comprising a transceiver configured to transmit the user biometric information to a server or a user device.

4. The health management device of claim 1, wherein the second threshold is greater than the first threshold.

5. The health management device of claim 1, wherein the interior surface comprises an adhesive material.

6. The health management device of claim 1, wherein the interior surface is configured to be to be adhered to user skin by using a belt.

7. The health management device of claim 1, wherein the exterior surface comprises a visual indication portion configured to receive a visual indicator indicating a user health condition.

8. The health management device of claim 7, wherein the visual indication portion comprises at least one of: a magnetic substrate, an adhesive substrate, and a fastening mechanism.

9. A health management method for a user comprising:
obtaining, by a processor, user biometric information from a sensor, wherein the sensor is disposed at an interior surface of a flexible body, and wherein the interior surface is configured to be adhered to user skin;

determining, by the processor, a user contraction level based on the user biometric information;

determining, by the processor, that the user contraction level is greater than a first threshold;

transmitting, by the processor, a first activation signal to a pharmaceutical disbursement unit responsive to a determination that the user contraction level is greater than the first threshold, wherein the pharmaceutical disbursement unit is configured to disburse a first predefined quantity of medicine in the user skin responsive to receiving the first activation signal;

determining, by the processor, that the user contraction level is greater than a second threshold;

transmitting, by the processor, a notification to an external device responsive to a determination that the user contraction level is greater than the second threshold;

obtaining, by the processor, an input from the external device responsive to transmitting the notification; and transmitting, by the processor, a second activation signal to the pharmaceutical disbursement unit responsive to obtaining the input, wherein the pharmaceutical disbursement unit disburses a second predefined quantity of medicine in the user skin responsive to receiving the second activation signal.

10. The health management method of claim 9, wherein the user biometric information comprises at least one of: a user contraction intensity, a user heart rate, a user oxygen level, a user labor activity, a fetus heart rate, fetus visual and/or audio feed.

11. The health management method of claim 9 further comprising transmitting the user biometric information to a server or a user device.

12. The health management method of claim 9, wherein the second threshold is greater than the first threshold.

13. A non-transitory computer-readable storage medium in a distributed computing system, the non-transitory computer-readable storage medium having instructions stored thereupon which, when executed by a processor, cause the processor to:
obtain user biometric information from a sensor, wherein the sensor is disposed at an interior surface of a flexible body, and wherein the interior surface is configured to be adhered to user skin;

determine a user contraction level based on the user biometric information;

determine, that the user contraction level is greater than a first threshold;

transmit a first activation signal to a pharmaceutical disbursement unit responsive to a determination that the user contraction level is greater than the first threshold, wherein the pharmaceutical disbursement unit is configured to disburse a first predefined quantity of medicine in the user skin responsive to receiving the first activation signal;

determine that the user contraction level is greater than a second threshold;

transmit a notification to an external device responsive to a determination that the user contraction level is greater than the second threshold;

obtain an input from the external device responsive to transmitting the notification; and transmit a second activation signal to the pharmaceutical disbursement unit responsive to obtaining the input, wherein the pharmaceutical disbursement unit disburses a second predefined quantity of medicine in the user skin responsive to receiving the second activation signal.

* * * * *